(12) United States Patent
Miyamoto et al.

(10) Patent No.: US 12,068,013 B2
(45) Date of Patent: Aug. 20, 2024

(54) RADIATION IMAGE READING DEVICE

(71) Applicant: HAMAMATSU PHOTONICS K.K., Hamamatsu (JP)

(72) Inventors: Yuichi Miyamoto, Hamamatsu (JP); Masaomi Takasaka, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 0 days.

(21) Appl. No.: 17/735,444

(22) Filed: May 3, 2022

(65) Prior Publication Data

US 2022/0270646 A1 Aug. 25, 2022

Related U.S. Application Data

(63) Continuation of application No. 16/341,162, filed as application No. PCT/JP2017/036177 on Oct. 4, 2017, now Pat. No. 11,355,150.

(30) Foreign Application Priority Data

Oct. 13, 2016 (JP) ................................. 2016-201663

(51) Int. Cl.
  *G11B 7/1381* (2012.01)
  *G02B 5/22* (2006.01)
  *G02B 5/28* (2006.01)

(52) U.S. Cl.
  CPC ............ *G11B 7/1381* (2013.01); *G02B 5/226* (2013.01); *G02B 5/286* (2013.01)

(58) Field of Classification Search
  CPC ....... G11B 7/1381; G02B 5/226; G02B 5/286
  See application file for complete search history.

(56) References Cited

U.S. PATENT DOCUMENTS

| 4,302,671 A | 11/1981 | Kato et al. |
| 4,554,454 A | 11/1985 | Taniguchi |

(Continued)

FOREIGN PATENT DOCUMENTS

| CN | 1769927 A | 5/2006 |
| CN | 105122084 A | 12/2015 |

(Continued)

OTHER PUBLICATIONS

International Preliminary Report on Patentability mailed Apr. 25, 2019 for PCT/JP2017/036177.

(Continued)

*Primary Examiner* — Blake C Riddick
(74) *Attorney, Agent, or Firm* — Faegre Drinker Biddle & Reath LLP (57) ABSTRACT

A radiation image reading device includes: a light scanning unit; a light detection unit. Each of a transmittance when the excitation light reflected from the surface of the recording medium is transmitted through the optical filter and a transmittance when the signal light emitted from the surface of the recording medium at an angle larger than a predetermined angle with respect to a direction perpendicular to the scan line within the detection surface is transmitted through the optical filter is smaller than a transmittance when the signal light emitted from the surface of the recording medium at an angle smaller than the predetermined angle with respect to a direction perpendicular to the scan line within the detection surface is transmitted through the optical filter.

4 Claims, 10 Drawing Sheets

(56) References Cited

U.S. PATENT DOCUMENTS

| | | | |
|---|---|---|---|
| 4,800,276 A | 1/1989 | Noguchi | |
| 4,849,632 A * | 7/1989 | Watanabe | G03B 42/02 |
| | | | 250/586 |
| 4,922,102 A * | 5/1990 | Katayama | H04N 1/10 |
| | | | 250/585 |
| 4,922,103 A | 5/1990 | Kawajiri | |
| 4,926,045 A | 5/1990 | Hosoi et al. | |
| 4,931,642 A | 6/1990 | Hosoi et al. | |
| 5,138,161 A | 8/1992 | Miyagawa et al. | |
| 5,341,245 A | 8/1994 | Tamagawa | |
| 5,416,336 A | 5/1995 | Koivulehto | |
| 5,530,260 A * | 6/1996 | Arakawa | H04N 1/028 |
| | | | 250/580 |
| 5,534,710 A | 7/1996 | Suzuki | |
| 5,753,932 A | 5/1998 | Arakawa | |
| 6,376,856 B1 | 4/2002 | Katagiri | |
| 6,486,974 B1 | 11/2002 | Nakai et al. | |
| 6,495,849 B2 * | 12/2002 | Yasuda | G01T 1/2016 |
| | | | 250/584 |
| 7,053,397 B1 * | 5/2006 | Nishioka | G01N 21/6456 |
| | | | 250/586 |
| 2001/0028047 A1 | 10/2001 | Isoda | |
| 2001/0054683 A1 * | 12/2001 | Kohda | A61B 6/5258 |
| | | | 250/235 |
| 2002/0060303 A1 | 5/2002 | Yonekawa | |
| 2002/0096653 A1 * | 7/2002 | Karasawa | G01T 1/2014 |
| | | | 250/586 |
| 2002/0117640 A1 * | 8/2002 | Akimoto | G03B 42/08 |
| | | | 250/585 |
| 2002/0185620 A1 * | 12/2002 | Akimoto | G01T 1/2014 |
| | | | 250/585 |
| 2003/0020031 A1 * | 1/2003 | Otokuni | G01T 1/2014 |
| | | | 250/589 |
| 2004/0099827 A1 | 5/2004 | Yasuda | |
| 2004/0129904 A1 | 7/2004 | Kuwabara | |
| 2005/0274917 A1 * | 12/2005 | Ishisaka | G01N 23/04 |
| | | | 250/584 |
| 2008/0002240 A1 | 1/2008 | Suga | |
| 2010/0220370 A1 | 9/2010 | Ueno et al. | |
| 2013/0250030 A1 * | 9/2013 | Sandstrom | G03F 7/70291 |
| | | | 347/225 |
| 2017/0017023 A1 | 1/2017 | Sugiyama et al. | |

FOREIGN PATENT DOCUMENTS

| | | |
|---|---|---|
| CN | 105339843 A | 2/2016 |
| CN | 105764401 A | 7/2016 |
| CN | 106062591 A | 10/2016 |
| EP | 1403697 A1 | 3/2004 |
| EP | 1431778 A1 | 6/2004 |
| JP | S60-119166 A | 6/1985 |
| JP | 2000-002955 A | 1/2000 |
| JP | 2000-066316 A | 3/2000 |
| JP | 2001-201809 A | 7/2001 |
| JP | 2002-77548 A | 3/2002 |
| JP | 2002-90922 A | 3/2002 |
| JP | 2002-107848 A | 4/2002 |
| JP | 2003-098176 A | 4/2003 |
| JP | 2003-232733 A | 8/2003 |
| JP | 2018-061694 A | 4/2023 |
| WO | WO 2012/169447 | 12/2012 |
| WO | WO 2015/137084 A1 | 9/2015 |
| WO | WO 2016/114362 A1 | 7/2016 |

OTHER PUBLICATIONS

Hamamatsu Photonics K.K., "MPPC Multi-Pixel Photon Counter—Technical Information", https://ethz.ch/content/dam/ethz/special-interest/phys/particle-physics/precisionphysicsatlowenergy-dam/TeachingContent/ASL/mppc.pdf, Oct. 31, 2008, p. 1-p. 21, XP093052715.

* cited by examiner

RADIATION IMAGE READING DEVICE

TECHNICAL FIELD

An aspect of the present invention relates to a radiation image reading device.

BACKGROUND ART

A radiation image reading device including a light scanning unit which scans excitation light onto a surface of a recording medium having a radiation image recorded thereon and a light detection unit which detects signal light emitted from the surface of the recording medium by the scanning of the excitation light is known (for example, see Patent Literature 1).

CITATION LIST

Patent Literature

Patent Literature 1: Japanese Unexamined Patent Publication No. 2002-77548

SUMMARY OF INVENTION

Technical Problem

In the above-described radiation image reading device, a decrease in device size may be required in some cases. However, for example, when the light detection unit is disposed so that a distance from the surface of the recording medium decreases in order to realize a decrease in device size, there is a possibility that radiation image detection accuracy decreases.

Therefore, an object of an aspect of the invention is to provide a radiation image reading device capable of decreasing a device size and maintaining radiation image detection accuracy.

Solution to Problem

A radiation image reading device according to an aspect of the invention includes: a light scanning unit which scans excitation light to a surface of a recording medium having a radiation image recorded thereon along a scan line; a light detection unit which detects signal light emitted from the surface of the recording medium by the scanning of the excitation light within a detection surface intersecting the surface of the recording medium and including the scan line; and an optical filter which is disposed between the light detection unit and the surface of the recording medium, in which each of a transmittance when the excitation light reflected from the surface of the recording medium is transmitted through the optical filter and a transmittance when the signal light emitted from the surface of the recording medium at an angle larger than a predetermined angle with respect to a direction perpendicular to the scan line within the detection surface is transmitted through the optical filter is smaller than a transmittance when the signal light emitted from the surface of the recording medium at an angle smaller than the predetermined angle with respect to a direction perpendicular to the scan line within the detection surface is transmitted through the optical filter.

In the radiation image reading device, each of the transmittance when the excitation light reflected from the surface of the recording medium is transmitted through the optical filter and the transmittance when the signal light emitted from the surface of the recording medium at an angle larger than the predetermined angle is transmitted through the optical filter is smaller than the transmittance when the signal light emitted from the surface of the recording medium at an angle smaller than the predetermined angle is transmitted through the optical filter. Accordingly, it is possible to suppress a decrease in radiation image detection accuracy since the excitation light is incident to the light detection unit. Further, even when the light detection unit is disposed so that a distance from the surface of the recording medium decreases and the length of the light detection unit in a direction parallel to the scan line is limited in order to realize a decrease in device size, it is possible to suppress a decrease in radiation image detection accuracy since the signal light has a diverging angle. The reason why the radiation image detection accuracy decreases since the signal light has a diverging angle is as below. That is, since the signal light emitted from the surface of the recording medium has a diverging angle, when the light detection unit is disposed so that a distance from the surface of the recording medium decreases and the length of the light detection unit in a direction parallel to the scan line is limited in order to decrease the device size, for example, the entire signal light is incident to the light detection unit at the center portion of the scan line and the entire signal light is not incident to the light detection unit at both end portions of the scan line. That is, in the radiation image reading device, it is possible to suppress a difference in detection range of the signal light emitted from the surface of the recording medium at the center portion and both end portions of the scan line even when the device size decreases. As described above, according to the radiation image reading device, it is possible to decrease a device size and to maintain the radiation image detection accuracy.

In the radiation image reading device according to an aspect of the invention, when a scan region of the excitation light and a detection region of the signal light have a centering alignment relationship within the detection surface, an equation of $\theta = \tan^{-1}\{(W2-W1)/2D\}$ may be established on the assumption that a width of the scan region is indicated by $W1$, a width of the detection region is indicated by $W2$ ($>W1$), a distance between the scan region and the detection region is indicated by $D$, and the predetermined angle is indicated by $\theta$. According to this configuration, since the detection range of the signal light emitted from the surface of the recording medium is the same at the center portion and both end portions of the scan line, it is possible to more reliably suppress a decrease in radiation image detection accuracy.

In the radiation image reading device according to an aspect of the invention, the optical filter may include a glass plate, a first dielectric multilayer film formed on one surface of the glass plate, and a second dielectric multilayer film formed on the other surface of the glass plate, and each of a transmittance when the excitation light reflected from the surface of the recording medium is transmitted through the first dielectric multilayer film and the second dielectric multilayer film and a transmittance when the signal light emitted from the surface of the recording medium at an angle larger than the predetermined angle with respect to a direction perpendicular to the scan line within the detection surface is transmitted through the first dielectric multilayer film and the second dielectric multilayer film may be smaller than a transmittance when the signal light emitted from the surface of the recording medium at an angle smaller than the predetermined angle with respect to a direction perpendicular to the scan line within the detection surface is transmitted through the first dielectric multilayer film and the second dielectric multilayer film. According to this configuration, it is possible to easily and reliably obtain the optical filter having the above-described function.

The radiation image reading device according to an aspect of the invention may further include an optical element which is disposed between the surface of the recording medium and the optical filter and has a function of converges the excitation light reflected from the surface of the recording medium and the signal light emitted from the surface of the recording medium only within a surface perpendicular to the detection surface. According to this configuration, one including the plurality of photodetector elements arranged along a direction parallel to the scan line can be used as the light detection unit.

In the radiation image reading device according to an aspect of the invention, the light detection unit may include a plurality of photodetector elements arranged along a direction parallel to the scan line and the plurality of photodetector elements may be controlled as one channel. According to this configuration, it is possible to read the radiation image with a simpler configuration.

Advantageous Effects of Invention

According to an aspect of the invention, it is possible to provide a radiation image reading device capable of decreasing a device size and maintaining radiation image detection accuracy.

DESCRIPTION OF EMBODIMENTS

Hereinafter, an embodiment of the invention will be described in detail with reference to the drawings. Furthermore, the same reference numerals will be given to the same or corresponding parts of the drawings and a repetitive description thereof will be omitted.

Figure 1:
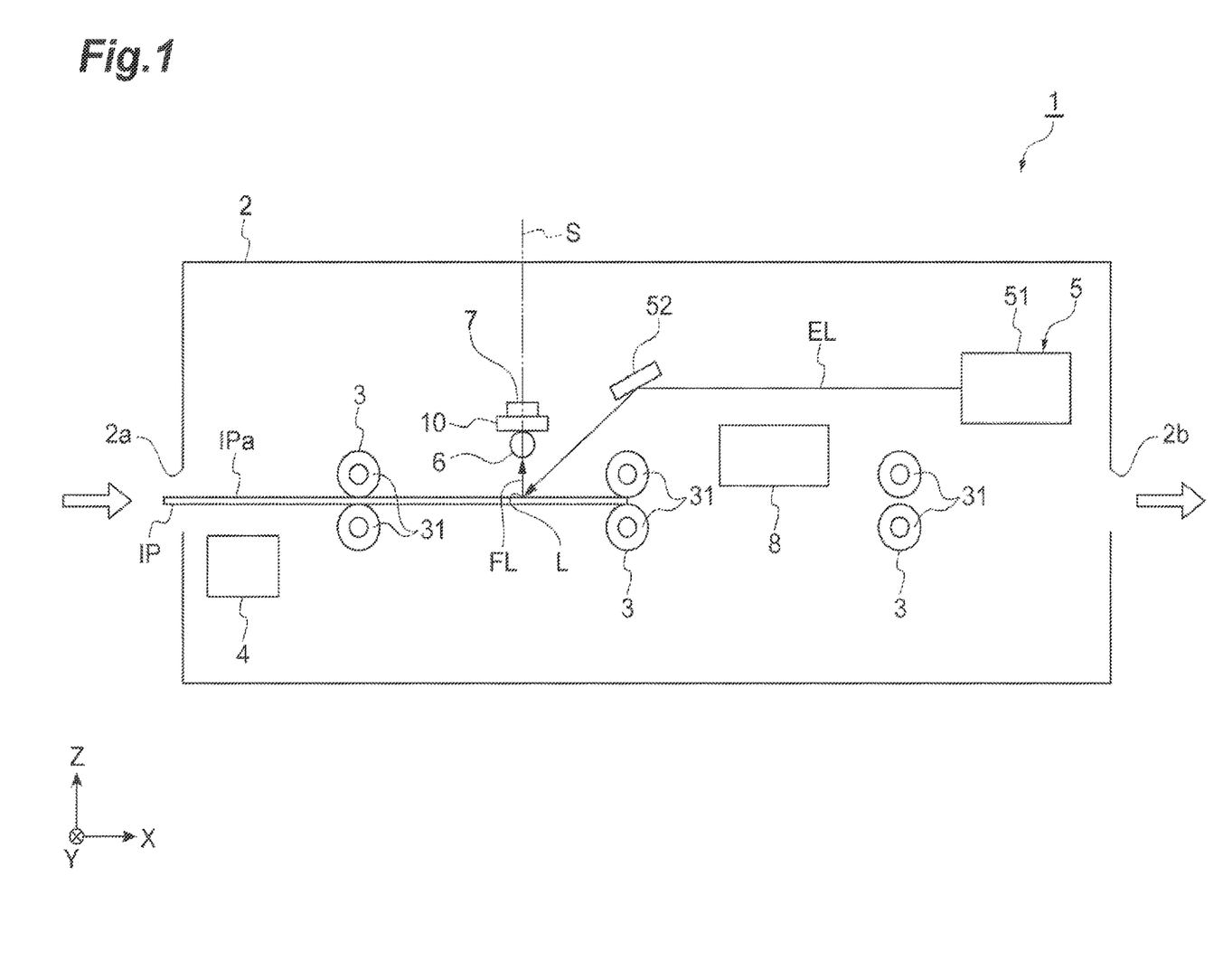
FIG. 1 is a configuration diagram of a radiation image reading device of an embodiment and is a diagram at the time of reading a radiation image.

As illustrated in FIG. 1, a radiation image reading device 1 includes a casing 2, a plurality of conveying roller pairs 3, a carry-in detection sensor 4, a light scanning unit 5, an optical element 6, an optical filter 10, a light detection unit 7, and a radiation image erasing unit 8. The radiation image reading device 1 is a device which reads a radiation image recorded on an imaging plate (a recording medium) IP.

The casing 2 accommodates the plurality of conveying roller pairs 3, the carry-in detection sensor 4, the light scanning unit 5, the optical element 6, the optical filter 10, the light detection unit 7, and the radiation image erasing unit 8. The casing 2 protects components accommodated in the casing 2 from the outside and shields light from the outside. The casing 2 is provided with an inlet 2a into which the imaging plate IP is conveyed and an outlet 2b from which the imaging plate IP is conveyed. The inlet 2a is provided in one wall portion of the casing 2 in the X-axis direction. The outlet 2b is provided in the other wall portion of the casing 2 in the X-axis direction.

The plurality of conveying roller pairs 3 are arranged along parallel in the X-axis direction to be separated from each other. A pair of rollers 31 constituting each conveying roller pair 3 extends along the Y-axis direction and faces each other in the Z-axis direction while being separated from each other. A gap between the pair of rollers 31 is substantially the same as the thickness of the imaging plate IP. The plurality of conveying roller pairs 3 are disposed so that the position of the gap between the pair of rollers 31 is substantially the same as the positions of the inlet 2a and the outlet 2b in the Z-axis direction. In the radiation image reading device 1, the imaging plate IP is conveyed from the inlet 2a, is conveyed along the X-axis direction by the plurality of conveying roller pairs 3, and is conveyed from the outlet 2b.

The carry-in detection sensor 4 is disposed in the vicinity of the inlet 2a of the casing 2. The carry-in detection sensor 4 detects whether the imaging plate IP is carried in when the imaging plate IP is carried in from the inlet 2a. As the carry-in detection sensor 4, for example, a mechanical switch (for example, Omron D2F-01FL-D3) may be used or a photodetector type sensor such as a photo interrupter may be used. Furthermore, it is desirable to use a mechanical switch when considering concern that the radiation image recorded on the imaging plate IP may be deteriorated due to the irradiation of the light emitted from the photodetector type sensor.

Figure 2:
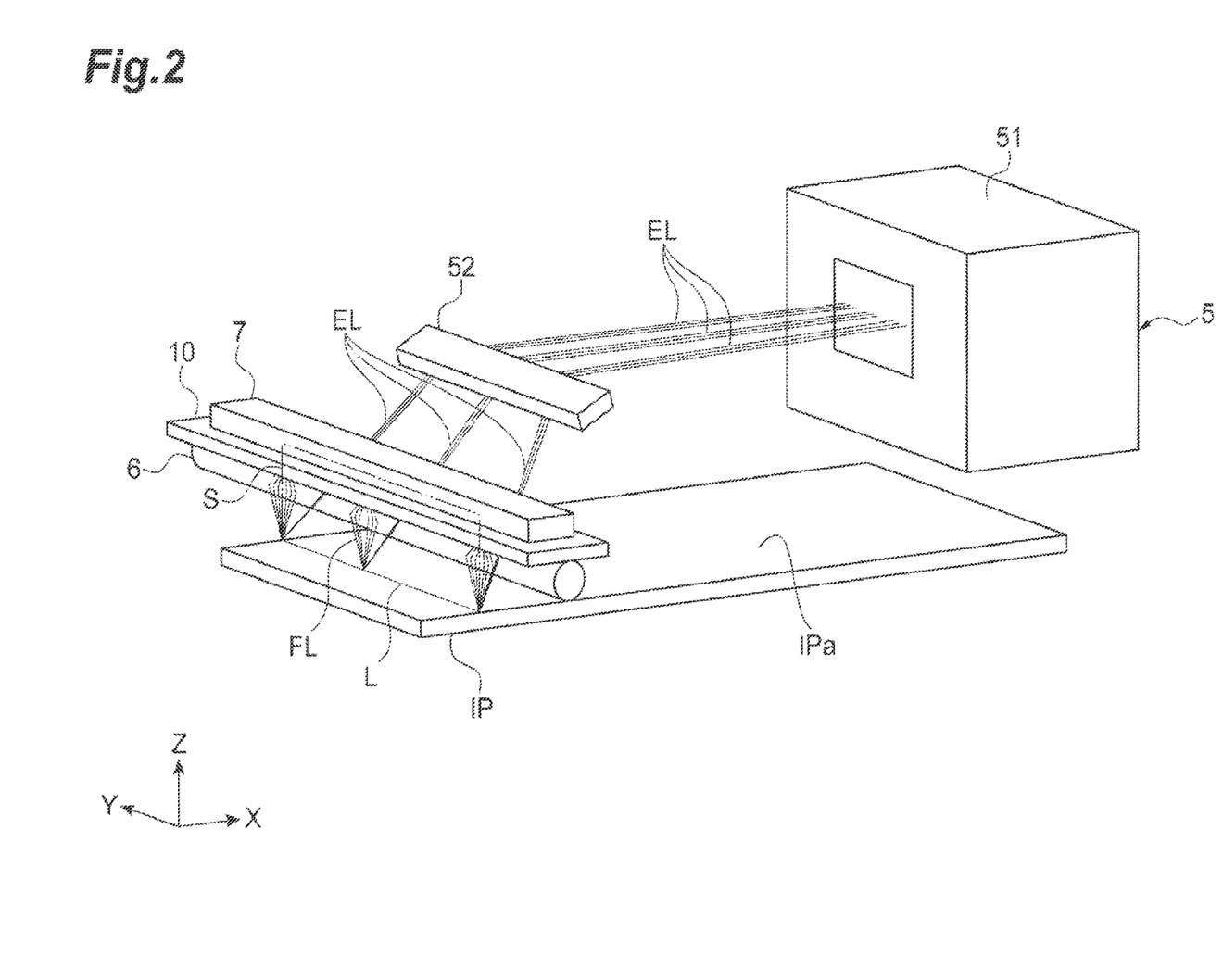
FIG. 2 is a perspective view of a part of the radiation image reading device of FIG. 1.

As illustrated in FIGS. 1 and 2, the light scanning unit 5 includes an excitation light source unit 51 and a position adjustment mirror 52. The excitation light source unit 51 includes an excitation light source (not illustrated) and a micro electro mechanical system (MEMS) mirror (not illustrated). The excitation light source unit 51 emits excitation light EL along the X-axis direction while swinging the excitation light EL about an axis parallel to the Z-axis direction. The position adjustment mirror 52 is configured to adjust the direction of a reflection surface about an axis parallel to the Y-axis direction. The position adjustment mirror 52 reflects the excitation light EL emitted from the excitation light source unit 51 to a scan line L. The scan line L is an imaginary line located on a surface IPa of the imaging plate IP (a surface recording the radiation image) conveyed by the plurality of conveying roller pairs 3 and is, for example, a line parallel to the Y-axis direction. In the radiation image reading device 1, the light scanning unit 5 scans the excitation light EL along the scan line L with respect to the surface IPa of the imaging plate IP recording the radiation image (that is, the irradiation region (the light collection region) of the excitation light EL is moved along the scan line L in a reciprocating manner).

The light detection unit 7 is disposed to face the scan line L in the Z-axis direction. The light detection unit 7 detects signal light FL emitted from the surface IPa of the imaging plate IP by the scanning of the excitation light EL within the detection surface S. The detection surface S is an imaginary plane which includes the scan line L and intersects the surface IPa of the imaging plate IP and is, for example, a surface which is parallel to the YZ plane.

Figure 3:
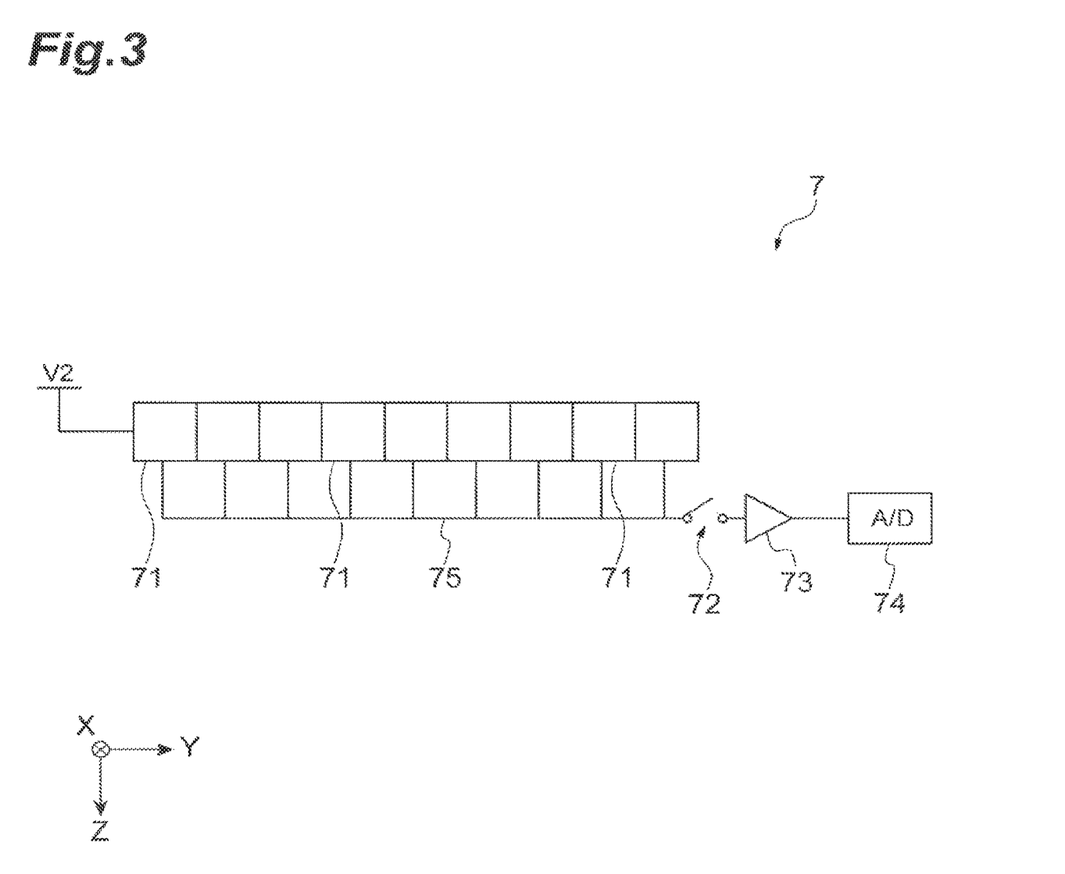
FIG. 3 is a configuration diagram of a light detection unit of the radiation image reading device of FIG. 1.

As illustrated in FIG. 3, the light detection unit 7 includes a plurality of photo diodes (photodetector elements) 71, a switch 72, an amplifier 73, and an A/D converter 74. The light detection unit 7 is, specifically, a MPPC (multi-pixel photon counter). The MPPC is a photon counting device which includes pixels of the plurality of photo diodes 71. The plurality of photo diodes 71 are arranged along the Y-axis direction (that is, a direction parallel to the scan line L). The plurality of photo diodes 71 are connected in parallel to one end of one switch 72 through a wire 75. The amplifier 73 is connected to the other end of the switch 72. The A/D converter 74 is connected to the amplifier 73. Furthermore, potentials having different polarities are applied to the photo diode 71. Among them, one potential V2 may be referred to as a ground potential.

When the signal light FL is incident to the light detection unit 7, each photo diode 71 outputs an electric signal in response to the light amount of the incident signal light FL. The electric signals output from the photo diodes 71 are added and are output to, for example, a control unit (not illustrated) through the amplifier 73 and the A/D converter 74. That is, the plurality of photo diodes 71 are controlled as one channel.

As illustrated in FIGS. 1 and 2, the optical filter 10 is disposed between the scan line L and the light detection unit 7. That is, the optical filter 10 is disposed between the light detection unit 7 and the surface IPa of the imaging plate IP conveyed by the plurality of conveying roller pairs 3. The optical filter 10 attenuates the excitation light EL reflected from the surface IPa of the imaging plate IP. Further, the optical filter 10 attenuates the signal light FL emitted from the surface IPa of the imaging plate IP at an angle larger than a predetermined angle with respect to a direction perpendicular to the scan line L within the detection surface S and transmits the signal light FL emitted from the surface IPa of the imaging plate IP at an angle smaller than the predetermined angle with respect to a direction perpendicular to the scan line L within the detection surface S. Furthermore, the optical filter 10 transmits the signal light FL emitted from the surface IPa of the imaging plate IP at a predetermined angle with respect to a direction perpendicular to the scan line L within the detection surface S.

Here, the "case of attenuating the excitation light EL reflected from the surface IPa of the imaging plate IP" means a case in which the transmittance when the excitation light EL is transmitted through the optical filter 10 is less than 50% on average. The "case of attenuating the signal light FL emitted from the surface IPa of the imaging plate IP at an angle larger than the predetermined angle with respect to a direction perpendicular to the scan line L within the detection surface S" means a case in which the transmittance when the signal light FL is transmitted through the optical filter 10 is less than 50% on average. The "case of transmitting the signal light FL emitted from the surface IPa of the imaging plate IP at an angle smaller than the predetermined angle with respect to a direction perpendicular to the scan line L within the detection surface S" means a case in which the transmittance when the signal light FL is transmitted through the optical filter 10 is 50% or more on average.

Figure 4:
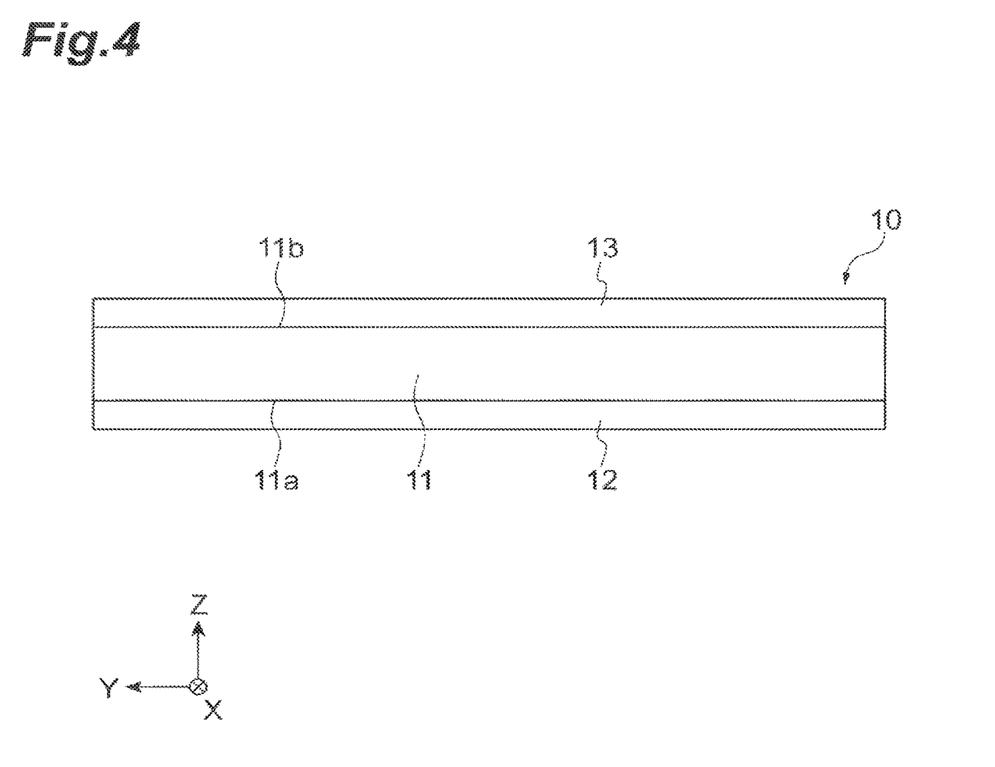
FIG. 4 is a configuration diagram of an optical filter of the radiation image reading device of FIG. 1.

As illustrated in FIG. 4, the optical filter 10 includes a glass plate 11, a first dielectric multilayer film 12, and a second dielectric multilayer film 13. The glass plate 11 includes a first surface (one surface) 11a and a second surface (the other surface) 11b which face each other in the Z-axis direction. The first surface 11a is a surface on the side of the scan line L in the glass plate 11. The second surface 11b is a surface on the side of the light detection unit 7 in the glass plate 11. The glass plate 11 is a member that allows the signal light FL to be transmitted therethrough. The glass plate 11 is formed as a color glass having a property of absorbing the excitation light EL. The first dielectric multilayer film 12 is formed on the first surface 11a. The second dielectric multilayer film 13 is formed on the second surface 11b. Each of the first dielectric multilayer film 12 and the second dielectric multilayer film 13 is, for example, a lamination structure formed by alternately laminating SiO2 and Ta2O5. The first dielectric multilayer film 12 and the second dielectric multilayer film 13 are respectively formed on the first surface 11a and the second surface 11b of the glass plate 11 by, for example, sputtering or vapor-depositing.

In the optical filter 10, the first dielectric multilayer film 12 and the second dielectric multilayer film 13 attenuate the excitation light EL reflected from the surface IPa of the imaging plate IP conveyed by the plurality of conveying roller pairs 3 and the signal light FL emitted from the surface IPa of the imaging plate IP at an angle larger than the predetermined angle with respect to a direction perpendicular to the scan line L within the detection surface S and allows the signal light FL emitted from the surface IPa of the imaging plate IP to be transmitted at an angle smaller than the predetermined angle with respect to a direction perpendicular to the scan line L within the detection surface S.

Figure 5:
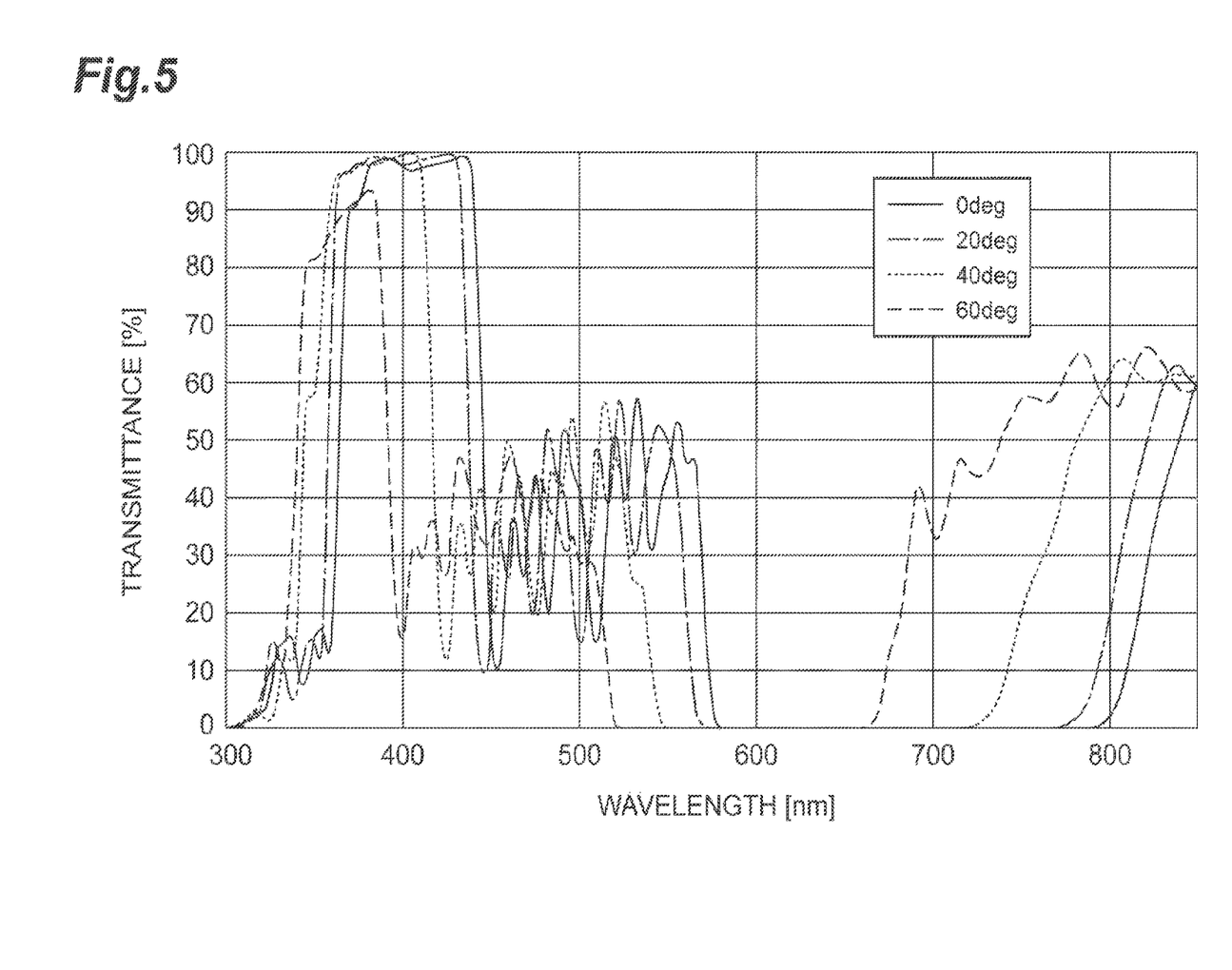
FIG. 5 is a diagram illustrating a transmittance characteristic with respect to an embodiment of an optical filter of FIG. 4.

FIG. 5 is a diagram illustrating a transmittance characteristic of an embodiment of the optical filter 10. The inventors have investigated the transmittance of the light when light of various wavelengths is incident to the optical filter 10 at an angle (here, referred to as an "incident angle") with respect to a direction perpendicular to the scan line L within the detection surface S in an embodiment of the optical filter 10. As illustrated in FIG. 5, the transmittance is substantially 0 regardless of the incident angle at the wavelength of 650 nm corresponding to the wavelength of the excitation light EL. Further, at the wavelength of 400 nm corresponding to the wavelength of the signal light FL, the transmittance was higher than 95% at the incident angle of 0°, 20°, and 40° and the transmittance was lower than 20% at the incident angle of 60°. That is, according to an embodiment of the optical filter 10, it was found that an angle larger than 40° and smaller than 60° can be set to the above-described predetermined angle when the wavelength of the signal light FL is 400 nm.

As illustrated in FIGS. 1 and 2, the optical element 6 is disposed between the scan line L and the optical filter 10. That is, the optical element 6 is disposed between the optical filter 10 and the surface IPa of the imaging plate IP conveyed by the plurality of conveying roller pairs 3.

Figure 6:
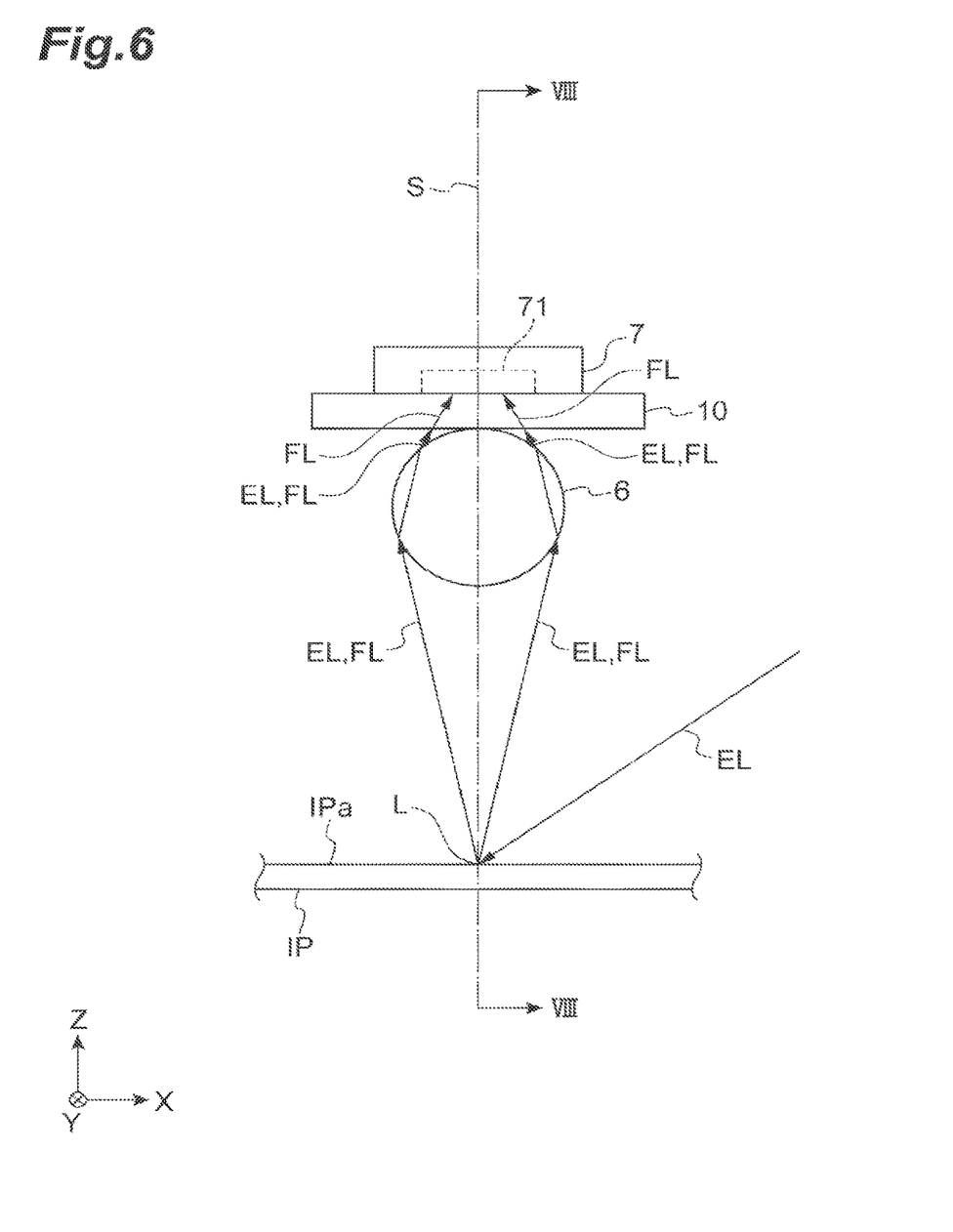
FIG. 6 is an enlarged view of a part of the radiation image reading device of FIG. 1.

As illustrated in FIG. 6, the optical element 6 is, for example, a rod lens having a columnar shape of which an axis parallel to the Y-axis direction is set as a center axis. Accordingly, the optical element 6 converges the excitation light EL and the signal light FL incident to the optical element 6 onto a line where the plurality of photo diodes 71 are arranged within a plane parallel to the ZX plane. On the other hand, the optical element 6 allows the excitation light EL and the signal light FL incident to the optical element 6 to be incident to the plurality of photo diodes 71 while not substantially converging those lights within the detection surface S. That is, the optical element 6 has a function of converging the excitation light EL reflected from the surface IPa of the imaging plate IP and the signal light FL emitted from the surface IPa of the imaging plate IP only within a surface (that is, a surface parallel to the ZX plane) perpendicular to the detection surface S.

As illustrated in FIGS. 1 and 2, the radiation image erasing unit 8 is disposed on the downstream side of the scan line L in the conveying direction of the imaging plate IP. The radiation image erasing unit 8 erases the radiation image from the surface IPa of the imaging plate IP, for example, by irradiating white light to the surface IPa of the imaging plate IP. As the radiation image erasing unit 8, for example, a white lamp such as a white LED (light emitting diode), a fluorescent lamp, or the like is used.

In the radiation image reading device 1 with the above-described configuration, the radiation image recorded on the imaging plate IP is read as below.

Figure 7:
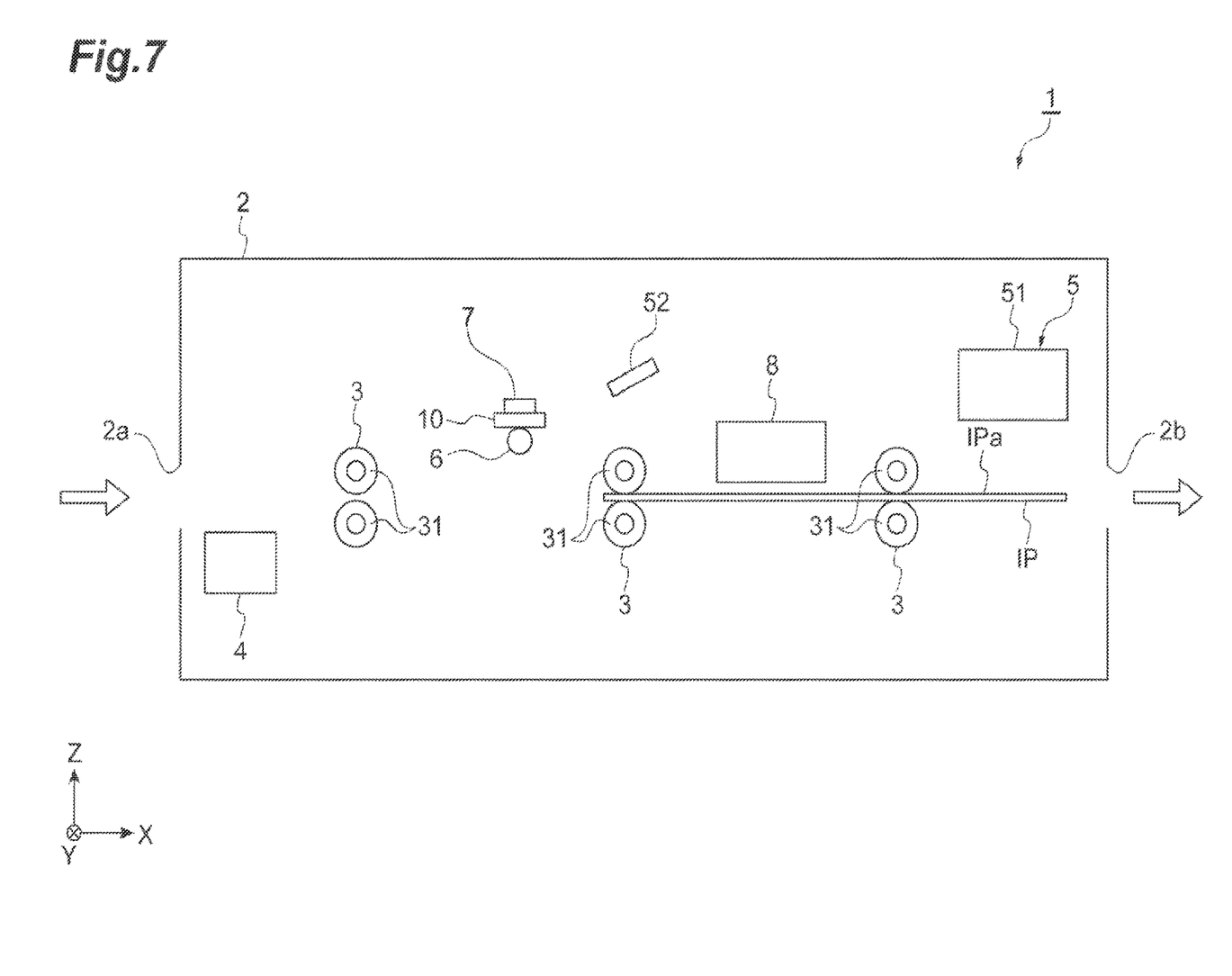
FIG. 7 is a configuration diagram of the radiation image reading device of FIG. 1 and is a diagram at the time of erasing a radiation image.

As illustrated in FIG. 1, the imaging plate IP is carried in from the inlet 2a into the casing 2 while the surface IPa of the imaging plate IP faces the light detection unit 7. At this time, the carried in of the imaging plate IP is detected by the carry-in detection sensor 4 and the operations of the conveying roller pair 3 and the light scanning unit 5 are started. The imaging plate IP which is conveyed into the casing 2 is conveyed by the conveying roller pair 3 along the X-axis direction. When the imaging plate IP is conveyed to a position facing the light detection unit 7, the light scanning unit 5 scans the excitation light EL along the scan line L with respect to the surface IPa of the imaging plate IP. The excitation light EL scanning the surface IPa of the imaging plate IP is reflected from the surface IPa of the imaging plate IP. At the same time, the signal light FL is emitted from the surface IPa of the imaging plate IP scanned by the excitation light EL. The light detection unit 7 detects the signal light FL transmitted through the optical element 6 and the optical filter 10. Then, as illustrated in FIG. 7, the imaging plate IP is conveyed out from the outlet 2b after the radiation image recorded on the surface IPa of the imaging plate IP is erased by the radiation image erasing unit 8. According to the radiation image reading device 1, it is possible to form the radiation image by irradiating the excitation light EL to the entire region where the radiation image is recorded on the surface IPa of the imaging plate IP and detecting the signal light FL in the entire region.

Next, a relationship between the scan region of the excitation light EL and the detection region of the signal light FL will be described.

Figure 8:
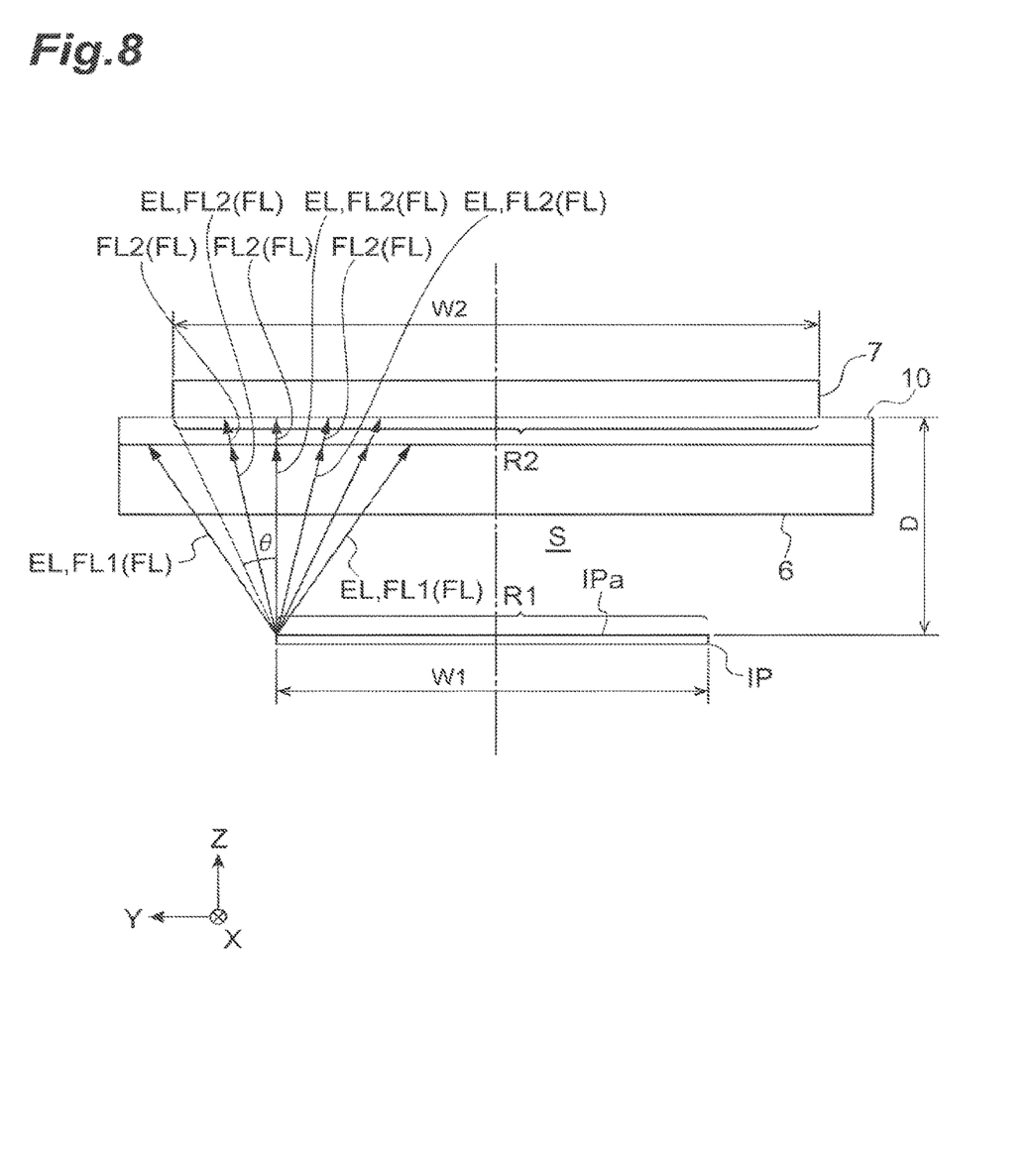
FIG. 8 is a cross-sectional view taken along a line VIII-VIII of FIG. 6.

As illustrated in FIG. 8, the width of the scan region R1 of the excitation light EL (the width in the Y-axis direction) within the detection surface S is W1. The scan region R1 of the excitation light EL means a range in which the surface IPa of the imaging plate IP is scanned by the excitation light EL within the detection surface S. That is, the width W1 of the scan region R1 of the excitation light EL is the same as the length of the scan line L within the detection surface S. The width of the detection region R2 of the signal light FL (the width in the Y-axis direction) within the detection surface S is W2. The detection region R2 of the signal light FL means a range in which light is detected by the light detection unit 7 within the detection surface S. That is, the same in the plurality of photo diodes 71 arranged along the Y-axis direction. The width W2 of the detection region R2 of the signal light FL is longer than the width W1 of the scan region R1 of the excitation light EL within the detection surface S. The scan region R1 of the excitation light EL and the detection region R2 of the signal light FL have a centering alignment relationship within the detection surface S. The centering alignment relationship means a state in which the center position of the scan region R1 of the excitation light EL (the center position in the Y-axis direction) and the center position of the detection region R2 of the signal light FL (the center position in the Y-axis direction) are aligned to each other in the Y-axis direction within the detection surface S. The distance between the scan region R1 of the excitation light EL and the detection region R2 of the signal light FL in the Z-axis direction is D. At this time, when the predetermined angle for the optical filter 10 is $\theta$, an equation of $\theta = \tan^{-1}\{(W2-W1)/2D\}$ is established.

As described above, in the radiation image reading device 1, the excitation light EL reflected from the surface IPa of the imaging plate IP is attenuated by the optical filter 10. That is, the excitation light EL reflected from the surface IPa of the imaging plate IP at an angle smaller than the predetermined angle $\theta$ with respect to a direction perpendicular to the scan line L within the detection surface S, the excitation light EL reflected from the surface IPa of the imaging plate IP at an angle larger than the predetermined angle $\theta$ with respect to a direction perpendicular to the scan line L within the detection surface S, and the excitation light EL reflected from the surface IPa of the imaging plate IP at the predetermined angle $\theta$ with respect to a direction perpendicular to the scan line L within the detection surface S are attenuated by the optical filter 10. Accordingly, it is possible to suppress a decrease in radiation image detection accuracy since the excitation light EL is incident to the light detection unit 7. Further, in the radiation image reading device 1, the signal light FL emitted from the surface IPa of the imaging plate IP at an angle larger than the predetermined angle $\theta$ is attenuated by the optical filter 10 and the signal light FL emitted from the surface IPa of the imaging plate IP at an angle smaller than the predetermined angle $\theta$ is transmitted through the optical filter 10. Accordingly, even when the light detection unit 7 is disposed so that a distance from the surface IPa of the imaging plate IP decreases and the length of the light detection unit 7 in a direction parallel to the scan line L is limited in order to decrease the device size, it is possible to suppress a decrease in radiation image detection accuracy since the signal light FL has a diverging angle. As described above, according to the radiation image reading device 1, it is possible to decrease the device size and to maintain the radiation image detection accuracy.

The reason why the radiation image detection accuracy decreases due to the diverging angle of the signal light FL is as below. That is, since the signal light FL emitted from the surface IPa of the imaging plate IP has the diverging angle, when the light detection unit 7 is disposed so that a distance from the surface IPa of the imaging plate IP decreases and the length of the light detection unit 7 in a direction parallel to the scan line L is limited in order to realize a decrease in device size, for example, the entire signal light is incident to the light detection unit 7 at the center portion of the scan line L and the entire signal light FL is not incident to the light detection unit 7 at both end portions of the scan line L (both end portions of the scan region R1 of the excitation light EL).

Specifically, as illustrated in FIG. 8, signal light FL1 traveling toward the other end portion of the scan line L with respect to a direction perpendicular to the scan line L between the signal light FL2(FL) emitted from the surface IPa of the imaging plate IP at an angle smaller than the predetermined angle θ with respect to a direction perpendicular to the scan line L and the signal light FL1(FL) emitted from the surface IPa of the imaging plate IP at an angle larger than the predetermined angle θ with respect to a direction perpendicular to the scan line L, for example, at one end portion of the scan line L within the detection surface S is incident to the light detection unit 7. On the other hand, the signal light FL1 traveling toward the opposite side to the other end portion of the scan line L with respect to a direction perpendicular to the scan line L in the signal light FL1(FL) emitted from the surface IPa of the imaging plate IP at an angle larger than the predetermined angle θ with respect to a direction perpendicular to the scan line L is not incident to the light detection unit 7. As described above, a difference in detection range of the signal light FL emitted from the surface IPa of the imaging plate IP is generated at the center portion and both end portions of the scan line L.

As described above, in the radiation image reading device 1, the optical filter 10 attenuates the signal light FL1(FL) emitted from the surface IPa of the imaging plate IP at an angle larger than the predetermined angle θ with respect to a direction perpendicular to the scan line L. That is, in the radiation image reading device 1, it is possible to suppress a difference in detection range of the signal light FL emitted from the surface IPa of the imaging plate IP at the center portion and both end portions of the scan line L even when the device size decreases.

Figure 9:
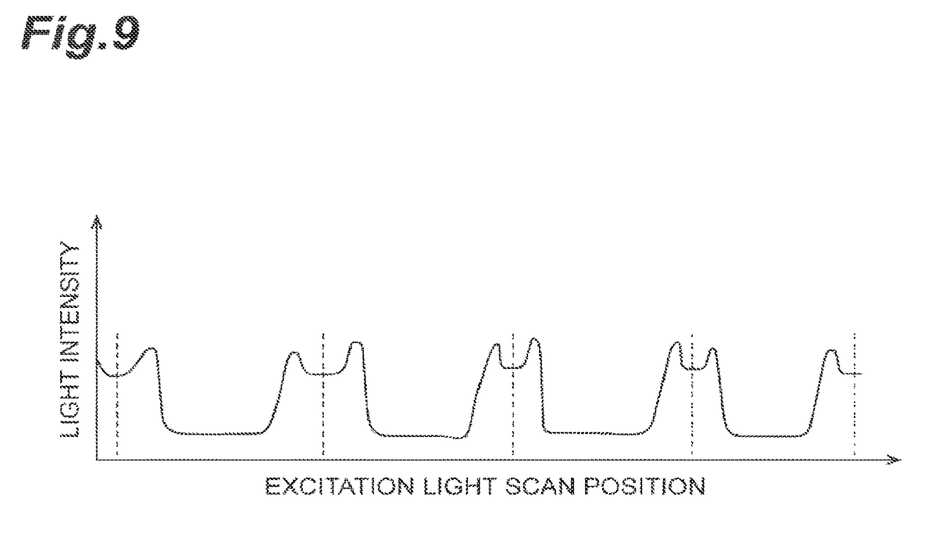
FIG. 9 is a diagram illustrating a light intensity distribution with respect to an excitation light scan position.

In a conventional radiation image reading device, there is a case in which the dielectric multilayer film that attenuates the excitation light EL reflected from the surface IPa of the imaging plate IP along a direction perpendicular to the scan line L within the detection surface S is employed as an excitation light cut filter. In such a case, the excitation light EL reflected from the surface IPa of the imaging plate IP at a predetermined angle with respect to a direction perpendicular to the scan line L within the detection surface S is not sufficiently attenuated. FIG. 9 is a diagram illustrating a light intensity distribution detected by the photo diode 71 disposed at the center of the light detection unit 7 in the Y-axis direction when such an excitation light cut filter is employed. Furthermore, FIG. 9 illustrates a light intensity distribution when the excitation light EL is scanned along the scan line L a plurality of times and a dashed line corresponds to a position facing the photo diode 71 disposed at the center (the scan position of the excitation light EL). In this case, the excitation light EL reflected from the surface IPa of the imaging plate IP at a predetermined angle with respect to a direction perpendicular to the scan line L within the detection surface S is incident to the light detection unit 7. For this reason, as illustrated in FIG. 9, the light intensity distribution detected by the photo diode 71 disposed at the center of the light detection unit 7 in the Y-axis direction increases at both sides in which the scan position of the excitation light EL is separated from the dashed line. In contrast, in the radiation image reading device 1, the optical filter 10 attenuates not only the excitation light EL reflected from the surface IPa of the imaging plate IP with respect to a direction perpendicular to the scan line L within the detection surface S but also the excitation light EL reflected from the surface IPa of the imaging plate IP at a predetermined angle with respect to a direction perpendicular to the scan line L within the detection surface S. Accordingly, it is possible to suppress an increase in light intensity distribution detected by the photo diode 71 disposed at the center of the light detection unit 7 in the Y-axis direction at both sides in which the scan position of the excitation light EL is separated from the dashed line.

Further, in the radiation image reading device 1, when the scan region R1 of the excitation light EL and the detection region R2 of the signal light FL have a centering alignment relationship within the detection surface S, an equation of $\theta = \tan^{-1}\{(W2-W1)/2D\}$ is established on the assumption that the width of the scan region R1 is indicated by W1, the width of the detection region R2 is indicated by W2 (>W1), the distance between the scan region R1 and the detection region R2 is indicated by D, and the predetermined angle is indicated by θ. According to this configuration, since the detection range of the signal light FL emitted from the surface IPa of the imaging plate IP is the same at the center portion and both end portions of the scan line L, it is possible to more reliably suppress a decrease in radiation image detection accuracy.

Further, in the radiation image reading device 1, the optical filter 10 includes the glass plate 11, the first dielectric multilayer film 12 formed on the first surface 11a of the glass plate 11, and the second dielectric multilayer film 13 formed on the second surface 11b of the glass plate 11. According to this configuration, it is possible to easily and reliably obtain the optical filter 10 having the above-described function. For example, when the first dielectric multilayer film 12 and the second dielectric multilayer film 13 are formed as below, the optical filter 10 has the above-described function. That is, the first dielectric multilayer film 12 may attenuate the signal light FL1(FL) emitted from the surface IPa of the imaging plate IP at an angle larger than the predetermined angle θ with respect to the scan line L within the detection surface S and the excitation light EL reflected from the surface IPa of the imaging plate IP at an angle smaller than the predetermined angle θ with respect to the scan line L within the detection surface S and the second dielectric multilayer film 13 may attenuate the excitation light EL reflected from the surface IPa of the imaging plate IP at an angle larger than the predetermined angle θ with respect to the scan line L within the detection surface S. In this way, in the dielectric multilayer film according to an aspect, the optical filter 10 having the above-described function can be obtained by combining two kinds or more of dielectric multilayer films when it is difficult to obtain the optical filter 10 having the above-described function. Furthermore, the functions of the first dielectric multilayer film 12 and the second dielectric multilayer film 13 are not limited to the above-described functions and the type of light to be attenuated by each of the first dielectric multilayer film 12 and the second dielectric multilayer film 13 can be arbitrarily set as long as the optical filter 10 having the above-described function can be obtained. Further, since the glass plate 11 is formed as a color glass having a property of absorbing the excitation light EL, the excitation light EL reflected from the first dielectric multilayer film 12 and the second dielectric multilayer film 13 inside the optical filter 10 is absorbed to the glass plate 11, it is possible to more reliably suppress a problem in which the excitation light EL is incident to the light detection unit 7. Further, the first dielectric multilayer film 12 and the second dielectric multilayer film 13 can be respectively stably formed on the first surface 11a and the second surface 11b of the glass plate 11.

Further, in the radiation image reading device 1, the optical element 6 having a function of converging the excitation light EL reflected from the surface IPa of the imaging plate IP and the signal light FL emitted from the surface IPa of the imaging plate IP only within a surface perpendicular to the detection surface S is disposed between the surface IPa of the imaging plate IP and the optical filter 10. According to this configuration, one including the plurality of photo diodes 71 arranged along a direction parallel to the scan line L can be used as the light detection unit 7.

Further, in the radiation image reading device 1, the plurality of photo diodes 71 arranged along a direction parallel to the scan line L in the light detection unit 7 are controlled as one channel. According to this configuration, it is possible to read the radiation image with a simpler configuration.

Although embodiments of the invention have been described, an aspect of the invention is not limited to the above-described embodiments.

In the above-described embodiment, the plurality of photo diodes 71 of the light detection unit 7 are controlled as one channel, but the plurality of photo diodes 71 may be controlled as a plurality of channels. Since the plurality of photo diodes 71 are controlled as a plurality of channels, it is possible to reduce noise as compared with a case in which the plurality of photo diodes 71 are controlled as one channel. Further, when the plurality of photo diodes 71 are controlled as a plurality of channels, even when the excitation light EL is not scanned along the scan line L, and the excitation light EL is scanned on the entire scan region R1, the radiation image recorded on the surface IPa of the imaging plate IP can be read.

Further, in the above-described embodiment, the transmittance when the "excitation light EL reflected from the surface IPa of the imaging plate IP" is transmitted through the optical filter 10 is less than 50% on average, the transmittance when the "signal light FL emitted from the surface IPa of the imaging plate IP at an angle larger than the predetermined angle with respect to a direction perpendicular to the scan line L within the detection surface S" is transmitted through the optical filter 10 is less than 50% on average, and the transmittance when the "signal light FL emitted from the surface IPa of the imaging plate IP at an angle smaller than the predetermined angle with respect to a direction perpendicular to the scan line L within the detection surface S" is transmitted through the optical filter 10 is 50% or more on average, but the values of the transmittance are not limited thereto. If each of the transmittance (for example, the transmittance on average) when the "excitation light EL reflected from the surface IPa of the imaging plate IP" is transmitted through the optical filter 10 and the transmittance (for example, the transmittance on average) when the "signal light FL emitted from the surface IPa of the imaging plate IP at an angle larger than the predetermined angle with respect to a direction perpendicular to the scan line L within the detection surface S" is transmitted through the optical filter 10 is smaller than the transmittance (for example, the transmittance on average) when the "signal light FL emitted from the surface IPa of the imaging plate IP at an angle smaller than the predetermined angle with respect to a direction perpendicular to the scan line L within the detection surface S" is transmitted through the optical filter 10, it is possible to decrease the device size and to maintain the radiation image detection accuracy. Here, since the excitation light EL is generally stronger than the signal light FL, it is desirable that the transmittance when the excitation light EL is transmitted through the optical filter 10 be less than 1% on average.

Further, in the above-described embodiment, the optical element 6 is formed in a columnar shape, but the shape of the optical element 6 does not matter as long as a function of converging the signal light FL emitted from the surface IPa of the imaging plate IP only within a plane perpendicular to the detection surface S is provided. Further, the optical element 6, the optical filter 10, and the light detection unit 7 may be in contact with one another (see FIG. 6) or may be separated from one another.

Figure 10A:
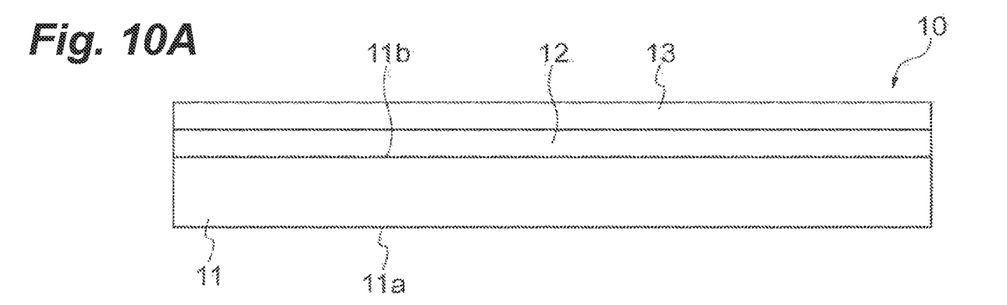
FIG. 10A is a configuration diagram of an optical filter of a first modified example.

Further, as illustrated in FIG. 10A, both the first dielectric multilayer film 12 and the second dielectric multilayer film 13 may be formed on the second surface 11b of the glass plate 11. Specifically, the first dielectric multilayer film 12 may be formed on the second surface 11b of the glass plate 11 and the second dielectric multilayer film 13 may be formed on the surface of the first dielectric multilayer film 12. Further, the second dielectric multilayer film 13 may be formed on the second surface 11b of the glass plate 11 and the first dielectric multilayer film 12 may be formed on the surface of the second dielectric multilayer film 13.

Figure 10B:
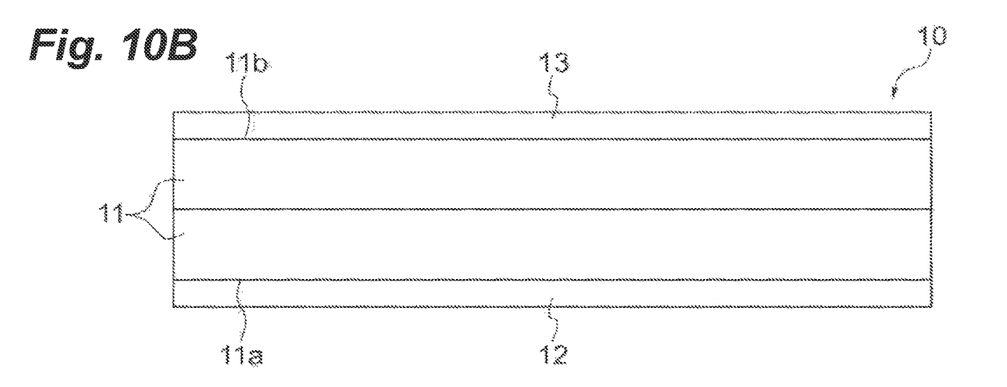
FIG. 10B is a configuration diagram of an optical filter of a second modified example.
Figure 10C:
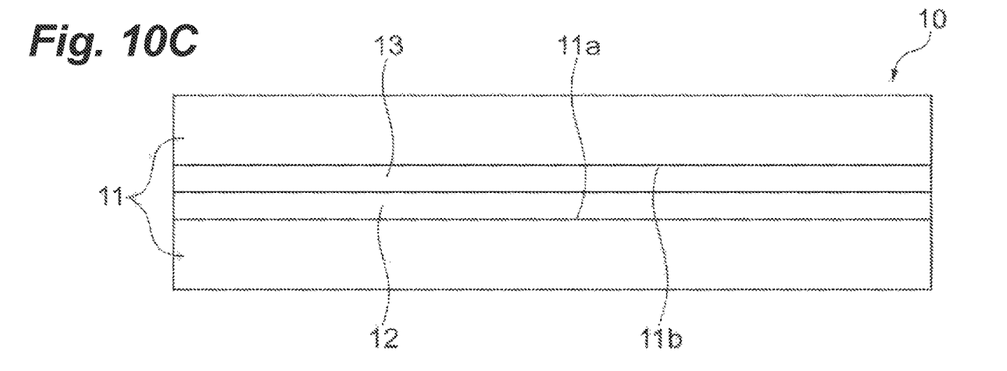
FIG. 10C is a configuration diagram of an optical filter of a third modified example.

Further, as illustrated in FIG. 10B, the optical filter 10 may include a plurality of glass plates 11. In this case, the first dielectric multilayer film 12 is formed on the surface 11a of one glass plate 11 and the second dielectric multilayer film 13 is formed on the surface 11b of the other glass plate 11. Then, the plurality of glass plates 11 are connected to each other to be interposed by the first dielectric multilayer film 12 and the second dielectric multilayer film 13. Further, as illustrated in FIG. 10C, the first dielectric multilayer film 12 and the second dielectric multilayer film 13 may be connected to each other to be interposed by the glass plate 11.

Further, in the above-described embodiment, the optical filter 10 transmits the signal light FL emitted from the surface IPa of the imaging plate IP at the predetermined angle θ with respect to a direction perpendicular to the scan line L within the detection surface S, but the optical filter 10 may attenuate the signal light FL emitted from the surface IPa of the imaging plate IP at the predetermined angle θ with respect to a direction perpendicular to the scan line L within the detection surface S.

Further, in the above-described embodiment, an equation of $\theta = \tan^{-1}\{(W2-W1)/2D\}$ is established in the optical filter 10, but the size of the predetermined angle θ can be set as required as long as the optical filter 10 can attenuate the excitation light EL reflected from the surface IPa of the imaging plate IP and the signal light FL1 (FL) emitted from the surface IPa of the imaging plate IP at an angle larger than the predetermined angle θ with respect to a direction perpendicular to the scan line L within the detection surface S. Furthermore, a decrease in radiation image detection accuracy is suppressed as the predetermined angle θ decreases.

Further, the predetermined angle θ can be recognized as below regardless whether the scan region R1 of the excitation light EL and the detection region R2 of the signal light FL have a centering alignment relationship within the detection surface S. Referring to FIG. 8, the predetermined angle θ can be recognized as an angle formed by an imaginary line connecting one end of the scan region R1 (one end in the Y-axis direction) and one end of the detection region R2 (one end in the Y-axis direction) with respect to a direction perpendicular to the scan line L within the detection surface S. Alternatively, the predetermined angle θ can be recognized as an angle formed by an imaginary line connecting the other end of the scan region R1 (the other end in the Y-axis direction) and the other end of the detection region R2 (the other end in the Y-axis direction) with respect to a direction perpendicular to the scan line L within the detection surface S. Furthermore, when the scan region R1 of the excitation light EL and the detection region R2 of the signal light FL do not have a centering alignment relationship, the predetermined angle θ is different at one side and the other side, but in that case, a small one between the predetermined angle θ at one side and the predetermined angle θ at the other side is desirably employed as the predetermined angle θ from the viewpoint of maintaining the radiation image detection accuracy.

Further, in the above-described embodiment, in the light detection unit 7, the plurality of photo diodes 71 are arranged along one dimension in the Y-axis direction, but the plurality of photo diodes 71 may be arranged in two dimensions within a plane parallel to the XY plane.

REFERENCE SIGNS LIST

1: radiation image reading device, 5: light scanning unit, 10: optical filter, 11: glass plate, 11*a*: first surface, 11*b*: second surface, 12: first dielectric multilayer film, 13: second dielectric multilayer film, 6: optical element, 7: light detection unit, 71: photo diode (photodetector element), EL: excitation light, FL: signal light, IP: imaging plate (recording medium), IPa: surface of imaging plate, L: scan line, R1: scan region, R2: detection region, S: detection surface, W1: width of scan region, W2: width of detection region, D: distance between scan region and detection region, θ: predetermined angle.

The invention claimed is:

1. A radiation image reading device comprising:
   a light scanning unit configured to scan excitation light along a scan line with respect to a surface of a recording medium having a radiation image recorded thereon; and
   a light detection unit configured to detect signal light emitted from the surface of the recording medium by the scanning of the excitation light within a detection surface including the scan line and intersecting the surface of the recording medium;
   wherein the light detection unit is a multi-pixel photon counter including a plurality of photodetector elements arranged along a direction parallel to the scan line,
   wherein electric signals output from the plurality of photodetector elements arranged along the direction parallel to the scan line are added and are output from the light detection unit, and
   wherein the light scanning unit is configured to move the spot-shaped excitation light along the scan line.

2. The radiation image reading device according to claim 1,
   wherein, within the detection surface, a width of a detection region of the signal light is longer than a width of a scan region of the excitation light in the surface of the recording medium.

3. The radiation image reading device according to claim 1, further comprising:
   an optical element is disposed between the light detection unit and the surface of the recording medium, and configured to allow the excitation light reflected from the surface of the recording medium and the signal light emitted from the surface of the recording medium to be incident to the light detection unit, the optical element converging the excitation light reflected from the surface of the recording medium and the signal light emitted from the surface of the recording medium within a surface perpendicular to the detection surface, and not converging the excitation light reflected from the surface of the recording medium and the signal light emitted from the surface of the recording medium within the detection surface.

4. The radiation image reading device according to claim 1, further comprising:
   an optical filter disposed between the light detection unit and the surface of the recording medium,
   wherein each of a transmittance when the excitation light reflected from the surface of the recording medium is transmitted through the optical filter and a transmittance when the signal light emitted from the surface of the recording medium at an angle larger than a predetermined angle with respect to a direction perpendicular to the scan line within the detection surface is transmitted through the optical filter is smaller than a transmittance when the signal light emitted from the surface of the recording medium at an angle smaller than the predetermined angle with respect to a direction perpendicular to the scan line within the detection surface is transmitted through the optical filter.

* * * * *